United States Patent
Wehowski et al.

(10) Patent No.: US 8,514,397 B2
(45) Date of Patent: Aug. 20, 2013

(54) METHOD FOR CONTROLLING A PHOTOMETRIC MEASURING UNIT OF A MEASURING DEVICE FOR OBTAINING AND EXAMINING A BODILY FLUID SAMPLE AND MEASURING SYSTEM

(75) Inventors: Frederic Wehowski, Hockenheim (DE); Herbert Harttig, Neustadt (DE); Joachim Hoenes, Zwingenberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/419,533

(22) Filed: Mar. 14, 2012

(65) Prior Publication Data
US 2012/0229810 A1 Sep. 13, 2012

Related U.S. Application Data

(63) Continuation of application No. PCT/EP2010/005679, filed on Sep. 16, 2009.

(30) Foreign Application Priority Data

Sep. 30, 2009 (EP) .................................... 09012364

(51) Int. Cl.
*G01N 33/48* (2006.01)
*G01N 21/00* (2006.01)

(52) U.S. Cl.
USPC ........................... 356/436; 356/39; 422/82.05

(58) Field of Classification Search
USPC ...................... 356/39, 436; 422/82.05, 82.09
See application file for complete search history.

(56) References Cited

U.S. PATENT DOCUMENTS

| 3,918,910 | A |   | 11/1975 | Soya et al. |
| 5,822,715 | A |   | 10/1998 | Worthington et al. |
| 5,889,585 | A |   | 3/1999 | Markart |
| 6,055,060 | A | * | 4/2000 | Bolduan et al. ................ 356/433 |
| 6,200,820 | B1 | * | 3/2001 | Hansen et al. ................ 436/523 |
| 6,249,593 | B1 |   | 6/2001 | Chu et al. |
| 7,758,812 | B2 | * | 7/2010 | Pachl et al. ................ 422/82.05 |
| 7,760,346 | B2 |   | 7/2010 | Effenhauser et al. |
| 7,889,329 | B2 | * | 2/2011 | Petrich et al. ................ 356/39 |

(Continued)

FOREIGN PATENT DOCUMENTS

EP  0 779 983 B2  6/1997

(Continued)

*Primary Examiner* — Roy M Punnoose
(74) *Attorney, Agent, or Firm* — Krieg DeVault LLP

(57) ABSTRACT

There is disclosed a method for controlling a photometric measuring unit of a measuring device for a bodily fluid sample, wherein a test field partially wetted by a bodily fluid sample is illuminated and light from a measuring area that covers a portion of the test field of the measuring unit is fed to a detector of the measuring unit, and the measuring area is displaced relative to the test field toward a partial surface wetted by the fluid sample and past the partial surface. The intensity of a detector signal is detected during the displacement, an extreme value in the course of the detector signal is determined, the measuring area is brought back to the position in which an extreme detector signal was previously measured, and the position of the measuring area in which the detector signal is extreme is used for a photometric determination of concentration.

15 Claims, 2 Drawing Sheets

(56) References Cited

U.S. PATENT DOCUMENTS

| | | |
|---|---|---|
| 2004/0225205 A1 | 11/2004 | Fine et al. |
| 2006/0018792 A1 | 1/2006 | Stock |
| 2009/0155921 A1 | 6/2009 | Lu et al. |
| 2009/0287116 A1 | 11/2009 | Konya |
| 2009/0304247 A1 | 12/2009 | Petrich et al. |

FOREIGN PATENT DOCUMENTS

| | | |
|---|---|---|
| EP | 0 922 054 B1 | 8/2002 |
| EP | 1 359 409 A2 | 11/2003 |
| EP | 1 775 577 A1 | 4/2007 |
| WO | WO 2008/083844 A1 | 7/2008 |
| WO | WO 2011/038839 A1 | 4/2011 |

* cited by examiner

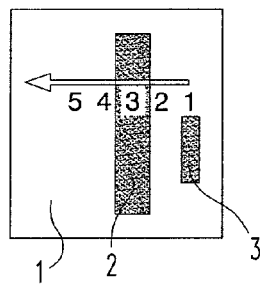
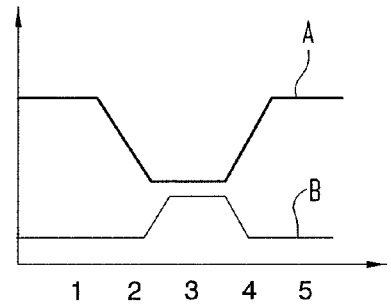
Fig. 1  Fig. 2
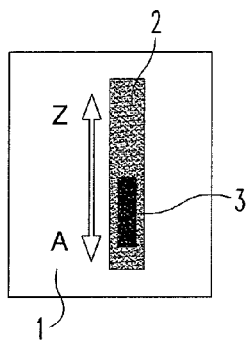
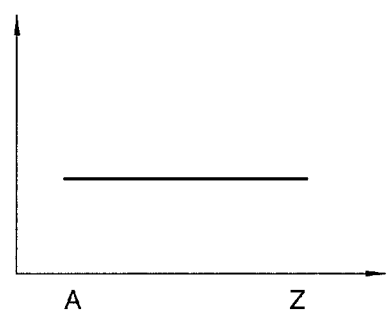
Fig. 3  Fig. 4
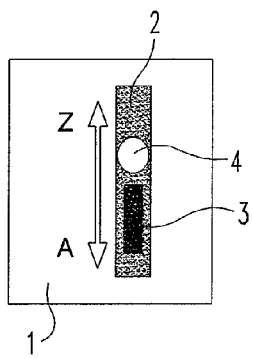
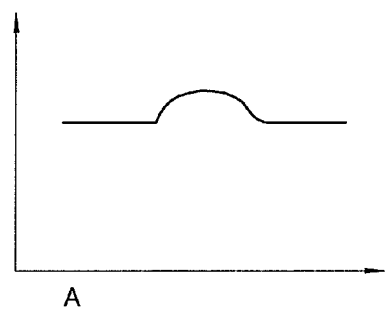
Fig. 5  Fig. 6

METHOD FOR CONTROLLING A PHOTOMETRIC MEASURING UNIT OF A MEASURING DEVICE FOR OBTAINING AND EXAMINING A BODILY FLUID SAMPLE AND MEASURING SYSTEM

CROSS-REFERENCE TO RELATED APPLICATIONS

This application is a continuation of International Application No. PCT/EP2010/005679 filed Sep. 16, 2010, which claims priority to EP Application No. 09012364.7 filed Sep. 30, 2009. Each of the referenced applications is incorporated herein by reference in its entirety.

FIELD OF THE INVENTION

The invention relates to a method for controlling a photometric measuring unit of a measuring device for examining a human or animal bodily fluid sample obtained by way of lancing. The invention further relates to a measuring system comprising a measuring device and test fields having detection reagents which induce a detection reaction upon contact with bodily fluid.

BACKGROUND

Detection reagents that can be evaluated photometrically typically induce a color change, the intensity of which depends on the analyte concentration. Such measuring systems make it possible to easily determine an analyte concentration in a bodily fluid sample, typically blood and/or interstital fluid. Important analyte concentrations that can be determined using such measuring systems are glucose concentration, cholesterol concentration, or lactate concentration, for example.

An advantage of a measuring and lancing device is that a bodily fluid sample obtained by way of lancing can be fed to a test field without any additional action on the part of a user. Lancing elements can be used, for example, which comprise a channel which takes up bodily fluid by way of capillary forces. Such a channel can lead to a test field disposed on the lancing element or can be used to transfer sample to a separate test field, e.g. by pressing a test field against a section of the channel designed as a groove. A further possibility for automatic sample take-up is known from WO 2008/083844 A1, for example, and involves placing a test field next to a lanced site using a suitable device mechanism.

Due to the automatic sample take-up, the operation of a measuring and lancing device is relatively simple and there is hardly any risk that a bodily fluid sample will become contaminated on the way to the test field. In addition, a concentration determination can be carried out even using very small sample quantities that are insufficient to wet a test field completely. To ensure that the photometric determination of concentration is not corrupted by light from unwetted test field regions, it is known from U.S. Pat. No. 6,249,593 to detect the test field using a detector array in a very large number of pixels and, by way of image evaluation, to remove pixels of unwetted regions to prevent interference signals. However, additional improvements in this area of technology are needed.

SUMMARY

The present invention provides is that of demonstrating a low-cost way to perform a photometric determination of concentration using small sample quantities that only partially wet a test field.

According to one aspect, there is disclosed a method for controlling a photometric measuring unit of a measuring device for examining a human or animal bodily fluid sample obtained by way of lancing. A test field that is partially wetted by a bodily fluid sample is illuminated and light from a measuring area that covers a portion of the test field is fed to a detector of the measuring unit. The measuring area is displaced relative to the test field toward a partial surface wetted by the bodily fluid sample and past the partial surface. During the displacement, the intensity of a detector signal is detected, an extreme value in the course of the detector signal is determined, the measuring area is brought again to the position in which an extreme detector signal was previously measured, and the position of the measuring area in which the detector signal is extreme is used for a photometric determination of concentration.

In another aspect for a method for controlling a photometric measuring unit of a measuring device, a test field partially wetted by a bodily fluid sample is illuminated and light from a measuring area that covers a portion of the test field is fed to a detector of the measuring unit.

In a further aspect, a system is disclosed for the photometric determination of an analyte concentration in a bodily fluid sample is disclosed. The system comprises test fields having detection reagents which, upon contact with bodily fluid, induce a detection reaction which can be evaluated photometrically. The system further includes a measuring device for measuring, by way of a test field, the analyte concentration in a bodily fluid sample obtained from a lanced site. The measuring device contains a measuring unit for performing a photometric measurement of a color change of a test field, the measuring unit has a light source and a detector, and the measuring unit defines a beam path for light from the light source to the detector. The beam path limits the sensitivity of the detector to a partial region of a test field fed to the measuring unit. The test field partial region from which the beam path directs light to the detector can be adjusted using at least one actuator. The actuator is controlled by a control unit which evaluates a detector signal and uses an actuator setting at which a detector signal is extreme for a photometric determination of concentration.

When concentration is measured on very small sample quantities, they are insufficient to wet a test field completely. Typically, test fields are wetted only partially by small sample quantities. This means that only a partial surface of a test field interacts with sample fluid and the remainder of the test field remains unwetted. Light from unwetted regions of the test field induces interference signals when a photometric measurement is carried out. Therefore, light from a measuring area that covers only a portion of the test field is fed to the detector of a measuring unit. According to one embodiment, the sensitivity of the detector is therefore limited to a partial region of a test field fed to the measuring unit.

To permit measurement of the color change of a partial surface of the test field wetted by bodily fluid, the measuring area must overlap with the wetted partial surface. According to another embodiment, the test field therefore searches for the bodily fluid sample by displacing the measuring area. During the displacement, the intensity of a detector signal is monitored to detect an extreme value. If an extreme value is found, this means that the measuring area has passed over the wetted partial surface of the test field.

That is, when the measuring area overlaps with the wetted partial surface of the test field, the detector signal changes markedly to an extent that increases as the overlap increases. If the detector signal is an extreme value, an advantageous setting having maximum overlap has therefore been attained.

To permit identification of an extreme value per se, the measuring area must be moved past the maximum overlap position to enable the detector signal to increase once more starting from a minimum value, for example. According to a further embodiment, the invention, the measuring area is therefore displaced toward the wetted partial surface and past the partial surface. In a refinement of this embodiment, the entire measuring area is displaced past the wetted partial surface to ensure that the measuring area no longer overlaps with the wetted partial surface. It is sufficient, however, to displace a portion of the measuring area past the wetted partial surface since even a reduction of the overlap between the measuring region and the wetted partial surface is sufficient to change the detector signal to an adequate extent, thereby permitting a previously attained extreme value to be identified per se.

The measuring area can therefore be positioned using the method described above on the partial surface of the test field that was wetted by the fluid sample by moving the optical measuring unit back into the position that resulted in the extreme detector signal.

Instead of measuring the entire test field using a detector array in a very large number of pixels and eliminating out pixels of unwetted regions, by way of image evaluation, to prevent interference signals, a measurement having comparable precision can be carried out using substantially simpler hardware.

Depending on the detector and the measurement principle, an overlap of the measuring area and the wetted partial surface of the test field can result in a reduced or elevated detector signal. If fluorescent light is evaluated, for example, the detector signal typically increases when the measuring area and the wetted partial surface of the test field overlap. In a remission measurement, by contrast, a lower light intensity is typically measured as soon as the measuring area overlaps with the wetted partial surface of the test field since this results in increased absorbance. The extreme value used can therefore be a maximum value or a minimum value.

To perform a photometric determination of concentration, the measuring area can be moved back and forth periodically on the test field, and so the measuring area periodically passes over the wetted partial region and a periodic detector signal is generated. The photometric determination of concentration can be carried out by evaluating the extreme signal intensities. One of the extreme values, such as the minimum value, occurs at maximum overlap between the measuring area and the wetted partial surface of the test field. The other extreme value occurs when the entire measuring area covers an unwetted partial region of the test field. The difference between the maximum and the minimum of the periodically changing detector signal therefore indicates the extent to which the remission and transmission properties of the test field have changed due to the wetting by the bodily fluid sample. Since the test field is illuminated with light, the absorbance of which by the test field is influenced by the color change induced by the detection reaction, the concentration of the bodily fluid sample can be determined photometrically on the basis of the difference of the extreme values of the periodically changing detector signal.

A lock-in amplifier can be used, advantageously, to evaluate a periodically changing detector signal. Such a lock-in amplifier can be implemented electronically. If the frequency is sufficiently high, the kinetics of the color change of the wetted test field region can also be detected. To this end, the frequency of the lock-in amplification should be selected to be clearly faster than the time resolution with which one wants to observe the kinetics, e.g. at least 100 Hz, in particular at least 500 Hz, preferably at least 1 kHz. The frequency range from 1 kHz to 10 kHz is suitable in particular.

As soon as a few extreme values of the periodically changing detector signal have been detected, the signal-to-noise ratio of the photometric measurement can be improved by feeding light to the detector only at the settings of the measuring unit that result in the extreme detector signal. This can be achieved, for instance, by rapidly switching a light source of the measuring unit on and off.

Instead of always illuminating the test field with the same light and, to perform the photometric determination of concentration, evaluating the difference between the maximum detector signal and the minimum detector signal that is generated when the measuring area covers the wetted partial surface or the measuring area covers an unwetted partial surface, respectively, the photometric determination of concentration can also be carried out by illuminating the test field for determining the extreme value of the detector signal with light having a spectral distribution other than that used for the photometric measurement to determine concentration.

As soon as it is determined—by evaluating the course of the detector signal on the basis of the extreme value—when the measuring area covers the wetted partial surface of the test field, the test field can be illuminated with light having a different spectral distribution for the photometric determination of concentration. Although light having a spectral distribution, the interaction of which with the test field is influenced practically not at all by the detection reaction, is particularly advantageous for locating the extreme value, light having a spectral distribution matched to the color change induced by the detection reaction is best suited for the photometric determination of concentration.

In principle, a different detector can be used for the photometric measurement than is used to position the measuring area. In one embodiment, the same detector is used for adjustment and for the photometric measurement to determine concentration. It is also possible to use two detectors, however, the sensitivity of which is limited to a partial region of a test field fed to the measuring unit, and to adjust the test field partial region from which light is fed to the detectors using at least one actuator, wherein the actuator is controlled by a control unit which evaluates a detector signal of a detector and uses an actuator setting for a photometric determination of concentration at which the detector signal of the other detector is an extreme value.

By illuminating the test field in an alternating manner with light having a different spectral distribution, moving the measuring area in a periodic manner permits different, alternating light to be used to illuminate the test field during the overlap of the measuring area and the wetted partial surface of the test field. A detector signal that was generated by light having the spectral distribution used to adjust the measuring unit can therefore be used to correct a measuring signal that was generated by light having the spectral distribution used for the photometric measurement.

This variant of the method can be implemented most easily by using a measuring unit having two different light sources, such as LEDs, which are switched on and off in alternation with the frequency of the back-and-forth motion. It is also possible, however, to use only one light source to which different color filters are connected.

An oscillating back-and-forth motion of the measuring area is suitable, in particular, when the wetted region of a test field is elongated, which can be the result of capillary channels, for example. A relatively long and narrow wetted region, such as a wetted region, the length of which is at least five times the width thereof, can be located reliably by moving the measuring area transversely to the longitudinal direction of the wetted region. It is also possible to sample the test field in a plurality of rows, although this is typically unnecessary if the used surface is sufficiently long.

In an alternative embodiment of the method, the measuring area is positioned on a wetted partial surface of the test field sample by displacing the measuring area into a position that results in the extreme detector signal and then a photometric measurement is performed in this position to determine concentration. In this manner, the measuring area can be positioned on the wetted partial surface of a test field by way of an adjustment motion, the adjustment motion can be stopped, and the photometric measurement can then be carried out.

In the case of an elongated wetting region of a test field in particular, which may result from capillary channels, for example, a motion of the measuring area in one spatial direction can suffice to attain a favorable adjustment of the measuring unit. The extreme value of the detector signal, which is found in this manner, may then be only a local maximum or minimum. In one embodiment, the measuring unit is adjusted by moving the measuring area in two spatial directions relative to the test field, e.g. by first setting an extreme detector signal by moving in a first spatial direction and then displacing the test field in a second spatial direction. The adjustment motion in the second spatial direction, as well as the adjustment motion in the second spatial direction, can be concluded and therefore stopped for a photometric measurement for concentration determination. It is also possible, however, to displace the measuring area back-and-forth in the second spatial direction for the photometric determination of concentration, and to determine the concentration by evaluating the resulting detector signal.

If the measuring area is thereby moved past the wetted partial region of the test field, a detector signal results that has periodically successive extreme values, which can be evaluated in the above-described manner to determine concentration. It may be advantageous, however, to move the measuring area back-and-forth to a lesser extent in order to displace it only on the wetted partial region. Uniform wetting then results in a constant detector signal since the entire measuring area always lies on the wetted partial region. In contrast, fluctuations in the detector signal indicate uneven wetting which can be due to air bubbles, for example. A non-uniform detector signal can signal to a user that concentration cannot be determined due to uneven wetting. In contrast, a constant detector signal can be used for a photometric determination of concentration.

In a further embodiment of the method, the displacement of the measuring area can be achieved by moving the test field or by moving one or more components of the measuring unit. These two possibilities for moving the measuring area relative to the test field can also be combined, e.g. by moving the test field to displace the measuring area in a first spatial direction, and by moving one or more components of the measuring unit to displace the measuring area in a second spatial direction which can be—but does not have to be—perpendicular to the first spatial direction.

In particular, a component of the measuring unit can be moved relative to the test field to displace the measuring area by moving a carrier of the measuring unit which carries one or more light sources and the detector or the detectors. In this manner, unwanted changes in imaging characteristics or illumination levels can be easily prevented, which is advantageous.

A device for moving a test field is typically present anyway in a measuring and lancing device, and so a positioning motion of the test field requires hardly any additional outlay. For example, test fields can be disposed on a carrier strip which can be wound in the forward direction and, optionally, in the backward direction for positioning in a manner similar to that of an audio cassette.

The method disclosed herein is suitable for transmission measurements and remission measurements.

According to a further embodiment, in order to adjust the measuring unit, the test field is illuminated with light having a spectral distribution different from that used for the photometric measure to determine concentration. To perform a photometric measurement to determine concentration, light is typically used that has an intensity largely in a spectral region in which the color change induced by a detection reaction takes place. If a detection reaction is used, for example, that results in increased absorbance in the blue color spectrum or the near UV range, then blue or UV light is best suited for the photometric measurement. In such a case, green light can be used, for example, to determine the setting of the measuring unit, the absorbance and remission of which is influenced practically not at all by the detection reaction.

By using light that interacts with the test field, e.g. by way of absorbance or remission, independently of the detection reaction for adjusting the measuring unit it is possible to start the adjustment of the measuring unit immediately after the test field is wetted, and to perform the adjustment while the detection reaction is underway.

In one embodiment of the method, light from a measuring area that covers a portion of the test field can be fed to the detector by focusing light onto the measuring area. A further possibility is to focus the detector on the measuring area.

In the first alternative mentioned, when the test field is illuminated, only the measuring area is illuminated while the remaining portion of the test field remains dark. In the second alternative, the entire test field is illuminated. To ensure that the detector is sensitive only to the measuring area, it must be ensured by way of suitable optical elements that light from test field regions outside of the measuring area does not reach the detector. These two variants are equivalent per se since it can always be ensured that light from only one measuring area reaches the detector, and they differ mainly only in the arrangement of optical components such as lenses or the like. In the first variant case, imaging takes place between the light source and the test field, in the second variant between the test field and the detector. If the description of the present invention mentions that the test field is illuminated, this includes the case in which only a portion of the test field is illuminated, i.e. the measuring area, and the case in which the entire surface of the test field is illuminated.

Detector signals practically always contain a noise component. To prevent delivering incorrect results due to a noise component of the detector signal, a threshold value for a signal level can be specified, and therefore an extreme value is handled as an extreme value only when the signal level observed thereby exceeds the threshold value.

BRIEF DESCRIPTION OF THE DRAWINGS

Further details and advantages of the invention are explained using an embodiment, with reference to the attached drawings.

FIG. 1 a schematic depiction of a test field comprising a wetted partial surface and a measuring area.

FIG. 2 a schematic depiction of the detector signal generated during displacement of the measuring area.

FIG. 3 the test field depicted in FIG. 1 having a measuring area positioned on the wetted partial surface.

FIG. 4 the graph of the detector signal during displacement of the measuring area when displacement occurs in the direction of the arrow shown in FIG. 3.

FIG. 5 a schematic depiction of a test field having a wetting defect.

FIG. 6 the graph of the signal during displacement of the measuring area shown in FIG. 5, in the direction of the arrow.

DETAILED DESCRIPTION

Figure 7:
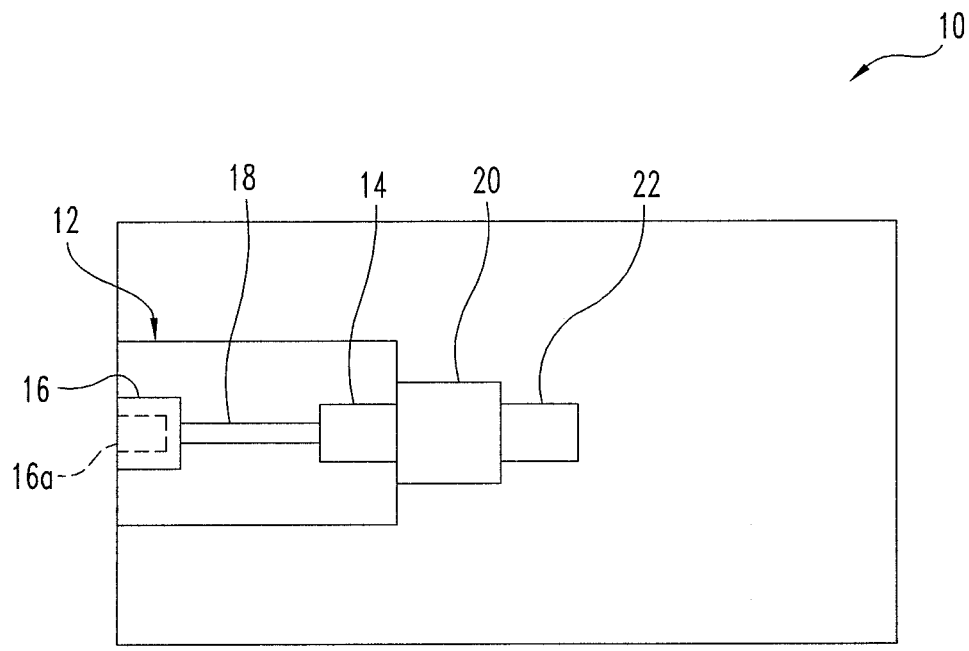
FIG. 7 is a block diagram of a measuring and lancing device.

For purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated device, and any further applications of the principles of the invention as illustrated therein being contemplated as would normally occur to one skilled in the art to which the invention relates.

FIG. 1 is a schematic depiction of a test field 1 which is wetted by a bodily fluid sample in a partial surface 2. The test field 1 contains detection reagents which, upon contact with a fluid sample, induce a detection reaction which brings about a color change of the wetted partial surface 2. The intensity of the color change depends on an analyte concentration being sought, such as glucose concentration. The analyte concentration being sought can therefore be determined by way of a photometric measurement.

Figure 8:
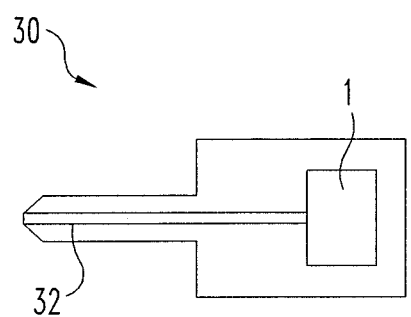
FIG. 8 is a diagrammatic illustration of a lancing element with a test field.

Such a test field 1, in combination with a lancing element 30 (FIG. 8) and a measuring and lancing device 10 (FIG. 7), forms a measuring system for the photometric determination of an analyte concentration in a bodily fluid sample. The test field 1 can be arranged on a lancing element 30 which comprises a channel 32 via which a sample can be transported to the test field by way of capillary forces. It is also possible to use separate lancing elements and test fields. A bodily fluid sample can be fed to a test field 1, e.g. by placing said test field next to a channel of a lancing element designed as a groove.

The measuring and lancing device 10 of such a measuring system contains a measuring unit 12 for the photometric measurement of a color change of a test field 1. The measuring unit 12, which is not shown, comprises a light source 14 and a detector 16 and defines a beam path 18 for light from the light source to the detector, and therefore the sensitivity of the detector 16 is limited to the measuring area 3, i.e. to a partial region of a test field 1 fed to the measuring unit 12. The beam path can be defined, for example, by a lens between the light source and the test field 1 or a lens between the detector and the test field 1.

The test field 1 is therefore illuminated and light from a measuring area 3 that covers a portion of the test field is fed to a detector 16 of a measuring unit 12. To perform a photometric determination of concentration, the test field 1 is wetted by bodily fluid on a partial surface 2 which is larger than the measuring area 3. In the embodiment shown, the dimensions of the partial surface 2 are approximately 200 µm by 1000 µm, while the dimensions of the measuring area are only 100 µm by 300 µm.

To permit a photometric measurement to determine concentration, the measuring area 3 must cover the partial surface 2 of the test field 1 that is wetted by the fluid. The test field 1 is therefore searched for the bodily fluid sample by displacing the measuring area 3.

Since the measuring area 3 is displaced in the direction of the arrow shown in FIG. 1, the wetted partial surface 2 is passed over by the measuring area, resulting in the course of a detector signal depicted schematically in FIG. 2. Various positions that result during displacement of the measuring area 3 in the direction of the arrow are labeled with numerals 1 to 5 in FIG. 1. The intensity of the detector signal at the corresponding positions is shown using curve A in FIG. 2.

If a remission measurement is carried out, as in the embodiment shown, the result is a significant reduction in signal intensity as soon as the measuring area 3 covers the partial surface 2 of the test field 1 wetted with the bodily fluid sample. The test surface 2 wetted by bodily fluid absorbs light to a markedly greater extent than do unwetted regions of the test field 1. The minimum of the signal graph A depicted in FIG. 2 therefore occurs when the entire measuring area 3 covers the wetted partial surface 2.

Instead of a remission measurement, it is also possible to determine concentration using fluorescent light. FIG. 2 shows a schematic depiction of the signal course for a fluorescent measurement as curve B. In this case the signal intensity increases as soon as the measuring area 3 covers the partial surface 2 of the test field 1 wetted by the bodily fluid sample since only wetted regions radiate fluorescent light.

The measuring area 3 can therefore be positioned on the wetted partial surface 2 of the test field 1 by moving the optical measuring unit 12 back into the position that resulted in the extreme detector signal. In the method described, the intensity of the detector signal is therefore detected during displacement of the measuring area 3 and an extreme value is subsequently determined on the basis of the course of the detector signal. Next, the measuring area 3 is displaced again into the position in which the extreme—minimal, for example—detector signal was previously observed.

The width of the partial surface 2 of the test field 1 wetted by the fluid sample can be determined from the course of the detector signal that is measured during displacement of the measuring area 3. This width can be compared to a setpoint value in order to detect wetting that is unsuitable for a determination of concentration. A deviation by more than a specified threshold value can be signaled to a user of the lancing and measuring device 10.

The test field 1 can be moved in order to displace the measuring area 3 relative to the test field 1. It is also possible, however, to displace the measuring area 3 by moving a component of the measuring unit 12. For example, a carrier of the measuring unit 12 which carries the detector 16 and the light source 14 can be displaced. Suitable actuators for moving a component of the measuring unit are known for write/read heads of CD drives or for digital cameras with shake reduction, for example. The actuator 20 is controlled by a control unit 22 of a measuring and lancing device 10, which evaluates a detector signal therefore and uses an actuator setting at which the detector signal is extreme to perform a photometric measurement of concentration.

Preferably, the distance between the detector 16 and the test field 1 as well as between the light source 14 and the test field 1 remains unchanged during displacement of the measuring area. Adjustment motions therefore preferably take place in only one or two spatial directions. Although an adjustment motion in three spatial directions is also possible, it is typically not required and would also increase the time required to determine concentration.

By bringing the optical measuring unit into the setting resulting in the extreme detector signal, the situation shown in FIG. 3 results, in which the measuring area 3 is placed within the wetted partial surface 2 of the test field 1. By displacing the measuring area 3 further in the direction of the arrow shown in FIG. 3, a check can be carried out to determine whether the test field 1 in the measuring area 3 is actually wetted completely and evenly with bodily fluid. Provided the partial surface 2 is wetted homogeneously as shown in FIG. 3, when the measuring area 3 is placed between positions A and Z in the arrow direction shown, the detector signal follows a constant course, as depicted schematically in FIG. 4.

Air bubbles or the like can result in underdosing with sample fluid and, therefore, inhomogeneous wetting. Such a case is depicted schematically in FIG. 5. In that case, the partial surface 3 is wetted incompletely by bodily fluid due to an air bubble 4. When the measuring area 3 is displaced in the direction of the double arrow shown, the signal course shown schematically in FIG. 6 therefore results. When the measuring area 3 covers a partial region that is wetted insufficiently due to an air bubble 4, less light is absorbed and remission therefore increases. By displacing the measuring area 3 transversely to a previous displacement in a first spatial direction, a check can therefore be carried out to determine whether the region of a test field 1 covered by the measuring area 3 in a selected measuring position is wetted completely with sample fluid.

In such a method, in order to determine an extreme value of a detector signal, such as a minimum value, the measuring area 3 is first displaced in a first direction and, after the measuring area 3 is positioned in the wetted partial surface 2, the measuring area is displaced transversely, in particular perpendicularly to the first direction, and, on the basis of the course of the intensity of the detector signal determined thereby, it is determined whether the wetted partial surface 2 is sufficiently large to accommodate the entire measuring area 3. If this is the case, the entire measuring area 3 is positioned in the wetted partial region 2 and a photometric determination of concentration is carried out; otherwise the user of the lancing and measuring device is notified by way of signaling that a determination of concentration cannot be carried out using the bodily fluid sample that was obtained.

The measuring area 3 can be displaced in the first direction by moving the test field 1, and the measuring area 3 can be displaced in the second direction by moving a component of the measuring unit 12, in particular a carrier of the measuring unit 12.

To determine the setting of the measuring unit 12 at which the detector signal is extreme, light can be used that has the same spectral distribution as for the photometric determination of concentration. A more reliable and faster adjustment of the measuring unit 12 can be achieved, however, by illuminating the test field 1 with light having a spectral distribution that is different from that used for the photometric measurement to determine concentration, in order to determine the setting of the measuring unit at which the detector signal is extreme. To adjust the measuring unit 12, light is preferably used, the absorbance of which by the test field 1 is practically uninfluenced by the detection reaction and the color change that is induced as a result. This has the advantage that an adjustment of the measuring unit 12 and, therefore, a positioning of the measuring area 3 within the wetted partial surface 2 can be easily carried out while the detection reaction is underway or even before it has started.

Light having a different spectral distribution can be generated, for example, by bringing appropriate color filters into the beam path. It is better, however, to use two different light sources, such as two LEDs, which emit light of a different color.

It is particularly advantageous to use a detector signal, generated by light having the spectral distribution used to adjust the measuring unit 12, for the correction of a measuring signal that was generated by light having the spectral distribution used for the photometric measurement. Light that is uninfluenced by the detection reaction can be used as a reference. This can be implemented most easily by switching the two light sources on and off in alternation, thereby feeding light having different spectral distributions to the detector in alternation after the measuring unit has been adjusted.

An alternative possibility for correcting a photometric measurement of the wetted partial surface 2 of the test field 1 is to use a measurement carried out using light having the same spectral distribution on an unwetted region of the test field 1 as a reference. The difference between the two signals obtained in this manner more accurately represents the intensity of the concentration-dependent color change of the wetted partial region 2 of the test field 1.

The two measurements can be carried out one after the other. It is also possible, however, to use a first detector for the photometric measurement and a further detector for a reference measurement on an unwetted partial region of the test field 1. In a corresponding measuring system, the measuring unit 12 therefore comprises at least one further detector 16a in addition to the detector 16, the detector signal of which is used for the adjustment of said measuring unit 12 and for a subsequent photometric determination of concentration on a bodily fluid sample. A measuring unit 12 can comprise three detectors, for example, wherein the middle detector is used for the photometric measurement and the other two detectors are each used for reference measurements on unwetted partial regions of the test field 1.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A method for controlling a photometric measuring unit of a measuring device for examining a human or animal bodily fluid sample obtained by way of lancing, wherein:
   a test field partially wetted by a bodily fluid sample is illuminated and light from a measuring area that covers a portion of the test field is fed to a detector of the measuring unit;
   the measuring area is displaced relative to the test field toward a partial surface wetted by the bodily fluid sample and past the partial surface;
   during the displacement, the intensity of a detector signal is measured and an extreme value in the course of the detector signal is determined;
   the measuring area is returned to a position in which the extreme value of the detector signal was previously measured; and
   the position of the measuring area in which the extreme value of the detector signal was measured is used for a photometric determination of analyte concentration.

2. The method according to claim 1, wherein the measuring area is positioned on the wetted partial surface of the test field by displacing the measuring area into the position in which the extreme value of the detector signal was previously measured, and then a photometric measurement is carried out to determine analyte concentration.

3. The method according to claim 1, wherein the measuring area is moved back and forth periodically on the test field such that the measuring area periodically passes over the wetted partial surface and a periodic detector signal is generated, wherein the photometric determination of analyte concentration is carried out by evaluating the intensity of the detector signal at the extreme value.

4. The method according to claim 2, wherein in order to determine the extreme value of the detector signal, the test field is illuminated with light having a spectral distribution that differs from a spectral distribution used for the photometric measurement to determine the analyte concentration.

5. The method according to claim 4, wherein a detector signal that was generated by light having the spectral distribution used to adjust the measuring unit is used to correct a measuring signal that was generated by light having the spectral distribution used for the photometric measurement.

6. The method according to claim 1, wherein the measuring area is displaced by moving a component of the measuring unit.

7. The method according to claim 1, wherein the measuring area is displaced by moving a carrier of the measuring unit which carries the detector and at least one light source.

8. The method according to claim 1, wherein the measuring area is displaced by moving the test field.

9. The method according to claim 1, wherein the measuring area is displaced in one direction by moving the test field, and is displaced in another direction by moving a component of the measuring unit.

10. The method according to claim 1, wherein the measuring unit performs a remission measurement.

11. The method according to claim 1, wherein the course of the detector signal measured during displacement of the measuring area is evaluated to determine whether the wetting is sufficient for a determination of concentration.

12. A measuring system for the photometric determination of an analyte concentration in a bodily fluid sample, comprising:
 test fields having detection reagents which, upon contact with bodily fluid, induce a detection reaction which can be evaluated photometrically; and
 a measuring device for measuring, by way of a test field, the analyte concentration in a bodily fluid sample obtained from a lanced site, wherein the measuring device includes a measuring unit for performing a photometric measurement of a color change of a test field, wherein the measuring unit has a light source and a detector, and the measuring unit defines a beam path for light from the light source to the detector, wherein the beam path limits the sensitivity of the detector to a partial region of a test field fed to the measuring unit, the test field partial region from which the beam path directs light to the detector is adjustable using at least one actuator, the actuator is controlled by a control unit which is operable to evaluate a detector signal and use an actuator setting at which the detector signal is extreme for a photometric determination of the analyte concentration.

13. The measuring system according to claim 12, wherein the lancing elements comprise a capillary channel that brings about the wetting of an elongated partial surface of a test field.

14. The measuring system according to claim 12, wherein the measuring unit comprises a plurality of light sources which are switched on in alternation by the control unit.

15. The measuring system according to claim 12, wherein the measuring unit comprises, in addition to the detector having the detector signal which is used for the adjustment of said measuring unit and for the subsequent photometric determination of concentration on a bodily fluid sample, a further detector for performing a reference measurement on an unwetted partial surface of the test field.

\* \* \* \* \*